United States Patent [19]

Kawai et al.

[11] Patent Number: 4,710,379

[45] Date of Patent: Dec. 1, 1987

[54] INTESTINAL MICROFLORA-IMPROVING AGENT

[75] Inventors: Yasuo Kawai, Atsugi; Hirotaka Shimohashi, Kodaira, both of Japan

[73] Assignee: Kabushiki Kaisya Advance Kaihatsu Kenkyujo, Tokyo, Japan

[21] Appl. No.: 938,348

[22] Filed: Dec. 4, 1986

Related U.S. Application Data

[63] Continuation of Ser. No. 737,057, May 23, 1985, abandoned.

[30] Foreign Application Priority Data

Jun. 19, 1984 [JP] Japan ................ 59-124584

[51] Int. Cl.$^4$ .............. A61K 35/74; A61K 35/78
[52] U.S. Cl. ..................... 424/93; 424/195.1
[58] Field of Search ............... 424/93, 195.1

[56] References Cited

U.S. PATENT DOCUMENTS

| | | | |
|---|---|---|---|
| 3,567,821 | 3/1971 | Nouvel | 424/93 |
| 3,729,554 | 4/1973 | Suzuki et al. | 424/93 |
| 4,259,442 | 3/1981 | Gayral | 435/14 |
| 4,448,768 | 5/1984 | Colman et al. | 424/92 |
| 4,579,733 | 4/1986 | Kawai et al. | 424/93 |
| 4,644,053 | 2/1987 | Brunelle et al. | 528/371 |

FOREIGN PATENT DOCUMENTS

| | | |
|---|---|---|
| 2106154 | 2/1971 | Fed. Rep. of Germany . |
| 0122723 | 3/1979 | Japan . |
| 930107 | 7/1963 | United Kingdom . |

OTHER PUBLICATIONS

Interration Reciept Forms, 1983.
K. Yazawa et al., Mech. of Ageing and Devel., 17(1981): 173–182.
K. Yazawa et al., Mech. of Ageing and Devel., 16(1981), 149–158.
Y. Kawai et al., Infection and Immun., 19(3): 771–778, 1978.
Y. Kawai, Am. J. Clin. Nat., 32(1979): 187–188.
D. Savage, Am. J. Clin. Nat., 25(1972): 1372–1379.
F. de Dombal et al., Gut 10(1969): 270–276.
T. Taniguchi et al., Microbiol Immunol., 22(12): 793–802, 1978.
E. Wolpert et al., Lancet, Dec. 25, 1971, 1387–1390.
A. Sato, Nat. Instit. of Animal Health, pp. 493–505.
Nord et al., "Formation of Glycoside . . . ", 1973, Archs. Oral Biol., vol. 18, pp. 391–402.
Watanabe et al., "Studies on Streptococci", 1981, Microbiol. Immun., vol. 25(3), pp. 225–269.
Kawai et al., "Studies on Streptococci", 1982, Microbiol. Immun., Vol. 26(5), pp. 363–373.
Kawai et al., "Distribution and Colonization . . . ", 1980, Am. J. of Clin. Nutr., vol. 33, pp. 2458–2461.
Kawai et al., "Intestinal Microflora and Aging . . . ", 1981, Mech. of Aging and Devl., vol. 16, pp. 149–158.
Moore et al., "Cell-Free Protein Synthesis . . . ", 1966, Science, vol. 154, pp. 1350–1353.
Herson et al., "Protein Synthesis in Cell-Free . . . ", 1969, J. of Bacteriology, vol. 100, No. 3, pp. 1350–1354.
Rao et al., "Influence of Milk and Themophilus . . . ", 1981, J. of Food Sci., vol. 46, pp. 1339–1341.
Salvioli et al., "Bile Acid Transformation . . . ", 1982, Digestion, vol. 23, pp. 80–88.
Hussain et al., "Activation of Lipolytic . . . ", 1976, Folia Microbiol., vol. 21, pp. 73–74.
Rall et al., "Human Apolopoprotein E", 1982, J. Biol. Chem., vol. 257(8), pp. 4171–4178.
Slobodskaya et al., "Comparison of hypoch . . . ", Biol. Abstract, 76(10).

*Primary Examiner*—J. R. Brown
*Assistant Examiner*—John W. Rollins
*Attorney, Agent, or Firm*—Finnegan, Henderson, Farabow, Garrett and Dunner

[57] ABSTRACT

An intestinal microflora-improving agent containing, as an effective component, bacterial cells and/or the water-soluble extracts therefrom, obtained from microorganisms belonging to the genus Streptococcus.

2 Claims, 21 Drawing Figures

INTESTINAL MICROFLORA-IMPROVING AGENT

This application is a continuation of application Ser. No. 737,057, filed May 23, 1985, now abandoned.

BACKGROUND OF THE INVENTION

1. Field of the Invention

The present invention relates to a new intestinal microflora-improving agent.

2. Description of the Related Art

It is said that there are about 100 trillion intestinal bacteria in the human intestines. These are classified into over 300 kinds. The significance of the intestinal microflora in humans has been revealed. For example, a fundamental investigation on relationships between intestinal bacteria and aging of the host has revealed that intestinal bacteria influence the activities of enzymes in various organs and the metabolism of important substances and that intestinal bacteria depress the accumulation of lipids and the inactivation of the detoxification function of the liver with aging (See Yazawa, K. et al. Mech. Ageing Devel. 17, 173 (1981), Kawai, Y. et al. Mech. Ageing Devel. 16, 149 (1981), Kawai, Y et al. Infect. Immun. 19, 771 (1978), and Kawai, Y am. J. of Clin. Nut 32, 187 (1979)). Many other studies on the importance of the intestinal microflora in hosts have been reported. (See Freter, R. Am. J. Clin. Nutr. 27, 1049 (1974), Gorbach, S. L. Gastroenterology, 60, 1110 (1971), Savage, D. C. Am. J. Clin. Nutr. 25, 1372 (1972), de Dombal, F. T., et al. Gut, 10, 270 (1969), Donaldson, R. M., Jr. New Engl. J. Med., 270, 938 (1964), Gordon, H. A., et al. Bacteriol. Rev., 35, 390 (1971), Taniguchi, T., et al. Microbiol. Immunol., 22, 793 (1978), Elyssen, H., Proc. Nutr. Soc., 32, 59 (1973), Wostmann, B. S. et al. J. Germfree Life Gnotobiol., 5, 4 (1975), Phear, E. A., et al. Br. J. Exp. Pathol., 37, 253 (1965), and Wolpert, E. et al. Lancet, ii, 1387 (1971)).

As evidenced by these studies, in many cases, the host's health is deteriorated by the abnormal overgrowth of harmful bacteria in the intestines. On the contrary, it is kept in a normal condition or is improved by the ordinary growth of useful intestinal bacteria such as Streptococcus, Lactobacillus, and Bifidobacterium. These facts strongly suggest that the selective growth of such useful intestinal bacteria in the intestines is quite important for the prevention and treatment of various kinds of so-called middle-aged or geriatric diseases.

SUMMARY OF THE INVENTION

Accordingly, the objects of the present invention are to suppress the abnormal over-growth of harmful bacteria in the intestines and to provide a novel intestinal microflora-improving agent capable of selectively stimulating the growth of useful microorganisms in the intestines.

Other objects and advantages of the present invention will be apparent from the following description.

In accordance with the present invention, there is provided an intestinal microflora-improving agent containing, as an effective component, bacterial cells and the water-soluble extracts therefrom, obtained from microorganisms belonging to the genus Streptococcus.

BRIEF DESCRIPTION OF THE DRAWING

The present invention will be better understood from the description set forth below with reference to the drawings, in which.

DESCRIPTION OF THE PREFERRED EMBODIMENTS

The inventors of the present invention have found in an investigation on the growth of Streptococcus, Lactobacillus, Bifidobacterium, etc. in the intestines that the bacterial cells or their water-soluble extracts obtained from bacteria belonging to the genus Streptococcus effectively stimulate the growth of those useful microorganisms.

The types and microbiological characteristics, the preparation procedures, the physiological activity, etc. of the intestinal microflora-improving agents according to the present invention will be explained in detail hereinbelow.

Microorganisms suitable for use in the preparation of the bacterial cell products according to the present invention are those belonging to the genus Streptococcus, especially Streptococcus faecalis, S. faecium, S. avium, S. salivarius, S. durans, S. mitis, S. bovis, and S. equinus.

Typical examples of such microorganisms have been deposited since July 15, 1982 in the Fermentation Research Institute (FRI) in Japan (all the numbers quoted as "FERM-P" in Table 1 refer to the deposition numbers of the Institute) and internally transferred in the FRI as an international depository authority under the Budapest Treaty (Budapest Treaty on the International Recognition of the Deposit of Microorganisms for the Purpose of Patent Procedure) under the FERM-BP deposition numbers in Table 1.

TABLE 1

| Strains | Deposition number | | |
|---|---|---|---|
| Streptococcus faecium | ADV1009 | FERM P-6624 | FERM BP-296 |
| Streptococcus faecalis | ADV9001 | FERM P-6625 | FERM BP-297 |
| Streptococcus avium | AD2003 | FERM P-6626 | FERM BP-298 |
| Streptococcus salivarius | ADV10001 | FERM P-6627 | FERM BP-299 |
| Streptococcus durans | ADV3001 | FERM P-6628 | FERM BP-300 |
| Streptococcus mitis | ADV7001 | FERM P-6629 | FERM BP-301 |
| Streptococcus equinus | ADV8001 | FERM P-6630 | FERM BP-302 |

The general microbiological characteristics of the microorganisms in the present invention are the same as those of known microorganisms belonging to the same class. That is, the general microbiological characteristics, cultivation method, and other properties correspond to those described in the following articles:

(1) Bergey's Manual of Determinative Bacteriology, 8th ed., 490–509 (1974)

(2) Int. J. Syst. Bacteriol. 16: 114 (1966).
(3) Microbiol. Immunol. 25: 257–269 (1981).
(4) J. Clin. Pathol. 33: 53–57 (1980).
(5) J. Gen. Microbiol. 128: 713–720 (1982).
(6) Appl. Microbiol. 23: 1131–1139 (1972).

The typical microbiological characteristics of the above-exemplified strains according to the present invention are summarized in Table 2.

TABLE 2

| Characteristics | ADV 1009 | ADV 9001 | AD 2003 | ADV 10001 | ADV 3001 | ADV 7001 | ADV 8001 |
|---|---|---|---|---|---|---|---|
| Shape of cell | | | | spheroid | | | |
| Gram stain | + | + | + | + | + | + | + |
| Hemolysis | α | α | α | α | α | α | α |
| Growth at | | | | | | | |
| 10° C. | + | + | ± | − | + | − | − |
| 45° C. | + | + | + | ± | + | ± | + |
| 50° C. | + | − | − | − | + | − | − |
| Thermal resistance at 60° C. for 30 min | + | + | + | − | + | − | − |
| Growth in culture medium at pH 9.6 | + | + | + | − | + | − | − |
| Methylene blue reduction | + | + | − | − | + | − | − |
| Liquefaction of gelatin | − | − | − | − | − | − | − |
| Growth in culture medium containing NaCl (6.5%) | + | + | − | − | + | − | − |
| Growth in culture medium containing bile (40%) | + | + | + | − | + | − | + |
| Productivity of ammonia | + | + | ND | − | + | ± | − |
| Hydrolysis of hippuric acid | − | ± | − | − | + | − | − |
| Growth in culture medium containing tellurite | − | + | − | ND | − | ND | − |
| Growth in culture medium containing TTC*1 | − | + | − | ND*2 | − | ND | − |
| Acid production from | | | | | | | |
| Glucose | + | + | + | + | + | + | + |
| Esculin | ± | + | + | + | ± | ND | + |
| Inulin | − | − | − | + | − | − | ± |
| Lactose | + | + | + | ± | + | ± | − |
| Glycerol | − | + | ± | − | − | − | − |
| Arabinose | + | − | + | − | − | − | − |
| Melezitose | − | + | ± | ND | − | ND | − |
| Sorbitol | − | + | + | − | − | − | − |
| Antigenic group | D | D | Q(D) | K | D | − | D |

*1: 2,3,5-Triphenyltetrazolium chloride
*2: Not done

Each strain of the above-mentioned microorganisms is inoculated into 5 L of Rogosa broth medium consisting of

| | |
|---|---|
| Trypticase (BBL) | 10 g |
| Yeast extract | 5 g |
| Tryptose | 3 g |
| KH$_2$PO$_4$ | 3 g |
| K$_2$HPO$_4$ | 3 g |
| Triammonium citrate | 2 g |
| Tween 80 | 1 g |
| Glucose | 20 g |
| Cysteine hydrochloride | 0.2 g |
| Salt solution *2 | 5 ml |
| Distilled water to | 1 liter |
| (pH 7, autoclave at 121° C for 15 min) | |

*2 MgSO$_4$—7H$_2$O  11.5 g
FeSO$_4$—7H$_2$O  0.68 g
MnSO$_4$—2H$_2$O  2.4 g
Distilled water  100 ml Each strain is then stationarily cultivated under an aerobic condition at 37° C. for 10 hrs to yield the subsequent culture broth containing 10$^9$ cells/ml of the viable cells. The microorganisms are harvested by continuous centrifugation at 12,000 rpm. The bacterial cells are washed with physiological saline and, then, are suspended in physiological saline (0.85% NaCl solution) to obtain 50 ml of the cell suspension containing 10$^{11}$ cells/ml.

The viable cells obtained are further washed twice with physiological saline and, then, are suspended in the same solution. Fifty ml of the cell suspension is thus obtained and is heated at 115° C. for 10 min to form the desired cell suspension containing the dead cells. This cell suspension is, then, lyophilized and dried in vacuo to obtain the dead cell powder.

The suspension of the above-mentioned bacterial cells, in distilled water or physiological saline (0.85% NaCl solution) containing 2×10$^{11}$ cells/ml, is autoclaved at 115° C. for 10 min to destroy the bacterial cells and to extract the hot-water soluble substances from the bacterial cells. The treated bacterial cell suspension is centrifuged at 2,000 G for 20 min to obtain the effective components in the supernatant of the present invention.

The above bacterial cell suspension is treated by sonication at 15 kc for 1 hr to destroy the bacterial cells and, then, the destroyed bacterial cell suspension is centrifuged at 20,000 to 25,000 G for 30 min to obtain the effective components in the supernatant of the present invention.

Distilled water, physiological saline, and various kinds of pH-adjusted buffers, etc. can be also used for the extraction.

The above-mentioned bacterial cells are heat-treated at 0° C. to 130° C., preferably at 80° C. to 120° C., for 10 min to several hours and, then, are centrifuged to obtain the effective components in the supernatant of the present invention.

The above-mentioned bacterial cells are treated singly with water and alcohol, such as methanol and ethanol, or with the mixture of these solvents and, then, are centrifuged to obtain the effective components in the supernatant of the present invention. The mixing ratios are usually water/alcohol=0/10 (v/v).

Methanol is removed from the supernatant when it is used as a solvent.

The effective components obtained by the above-mentioned procedures or by the combined procedures according to the present invention are used in the forms of liquid, lyophilized powder, powder dried in vacuo, etc.

The agents of the present invention selectively stimulate the growth of the useful intestinal bacteria. Such a physiological activity results in the effective improvement of the intestinal microflora. That is, the oral administration of the agents of the present invention into humans with abnormal intestinal microflora normalizes the population levels of useful intestinal bacteria such as Bifidobacterium, Lactobacillus, and Streptococcus, whereby the growth of these bacteria is stimulated to their normal levels. For example, as mentioned in the examples hereinbelow, the oral administration of the agents of the present invention can enhance the intestinal bacterial population levels to their normal levels (Bifidobacterium, ca. $10^8$ to $10^{11}$/g feces; Lactobacillus, about $10^5$ to $10^8$/ g feces; and Streptococcus, ca. $10^6$ to $10^8$/g feces) even in people whose population levels of Bifidobacterium, Lactobacillus, and Streptococcus are extremely lower than those of healthy people who have normal intestinal microflora.

As shown in the examples hereinbelow, the $LD_{50}$ values of the preparations composing the bacterial cells and the water-soluble extracts of the present invention were over $6 \times 10^9$ bacterial cells/mouse (intraperitoneal administration) and the amount equivalent to over $2.6 \times 10^{10}$ bacterial cells/mouse (intraperitoneal administration), respectively. Both the preparations were substantially nontoxic on oral administration.

The agents according to the present invention can be generally applied in a dose of $10^7$ to $10^{15}$ cells/kg body weight, more preferably $10^9$ to $10^{12}$ cells/kg body weight by, for example, oral administration. The agents according to the present invention can be made in the form of, for example, suspensions in physiological saline solutions, powder, granules, tablets, and capsules. The agents according to the present invention can be optionally prepared by using conventional appropriate carriers, bulk fillers, diluents, etc.

The present invention will now be further shown by, but is by no means limited to, the following examples.

EXAMPLE 1

Preparation of Bacterial Cells

Streptococcus faecalis ADV9001 was inoculated into the above-mentioned Rogosa broth medium (5 l) at a final concentration of $10^6$ viable cells/ml and was stationarily incubated at 37° C. for 10 hrs to yield $10^9$ cells/ml of the culture fluid. Then, the bacterial cells were collected by continuous centrifugation (12,000 rpm) of the culture fluid. The separated cells were washed twice with physiological saline (0.85% NaCl solution) by centrifugation. The centrifuged cells were then suspended in distilled water or physiological saline to obtain 50 ml of the cell suspension ($10^{11}$ cells/ml) and were autoclaved at 115° C. for 10 min. Finally, the heat-treated bacterial cell suspension was lyophilized to obtain the dead bacterial cell powder.

EXAMPLE 2

Growth-Stimulating Effect 1

The growth-stimulating effect of the agents obtained from the microorganisms exemplified below according to the present invention was examined in vitro. In this example, the lyophilized powder of the heat-treated cells of Streptococcus faecalis ADV9001 was used.

| | |
|---|---|
| Bifidobacterium adolescentis | RIMD 0232001 |
| Lactobacillus salivarius | An isolate from human intestine |
| Lactobacillus casei | IID892 |
| Lactobacillus acidophilus | IID893 |
| Streptococcus faecalis | ADV9001 |
| Streptococcus faecalis | ADV9002 |
| Streptococcus durans | ADV3001 |
| Streptococcus bovis | ADV4002 |
| Streptococcus faecium | ADV1003 |
| Streptococcus avium | ADV2002 |

The dead bacterial cell powder of S. faecalis ADV9001 was added into media shown in Table 3. The media were, then, autoclaved at 115° C. for 15 min. Each of the strains shown in Table 3 was then inoculated into the respective medium. The viable cell counts in the culture fluid were examined periodically. For a comparison with the dead bacterial cell powder of S. faecalis ADV9001, the heat-treated (115° C., 10 min) and lyophilized powder of Bacteroides fragilis ss. fragilis RIMD 0230001 and E. coli DEFINE (IAM) 1239, and commercial yeast extract were also examined as to their growth-stimulating effect on each strain shown in Table 3.

TABLE 3

| Microorganisms | Media |
|---|---|
| Bifidobacterium | VLG medium diluted 10-fold with phosphate buffered saline (PBS) |
| Lactobacillus | PBS supplemented with glucose (1 mg/ml) and Trypticase (5 mg/ml, BBL) |
| Streptococcus | PBS or PBS supplemented with glucose (1 mg/ml) |

The results were shown in FIGS. 1–15.

Figure 1:
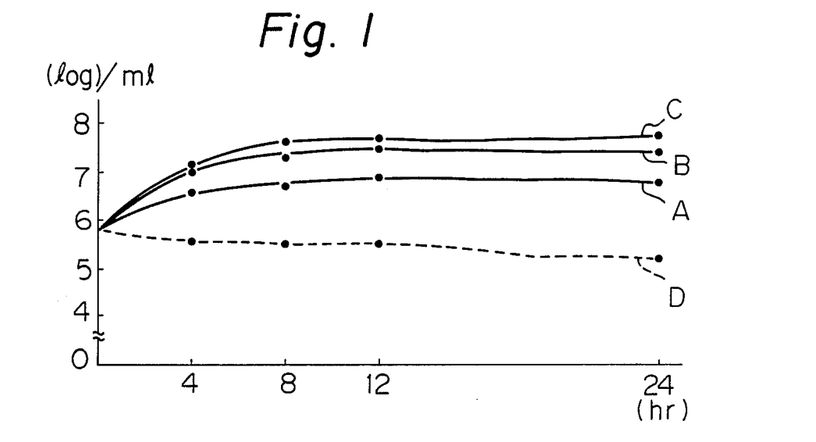
FIGS. 1 to 15 are graphical drawings illustrating the growth-stimulating effects of the lyophilized powder of the heat-treated cells of Streptococcus faecalis ADV 9001 on the growth of various microorganisms and FIGS. 16 to 18 are graphical drawings illustrating the growth-stimulating effects of the lyophilized powder of the heat-treated cells of Streptococcus faecium ADV-1009 on the growth of various microorganisms.
Figure 2:
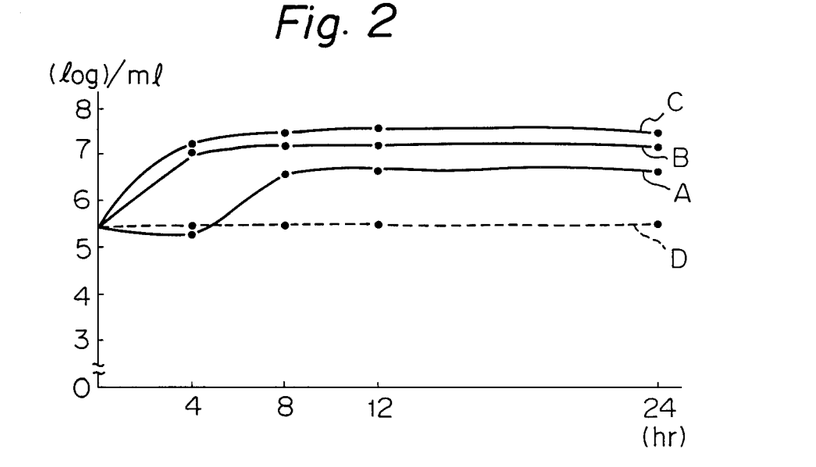
Figure 3:
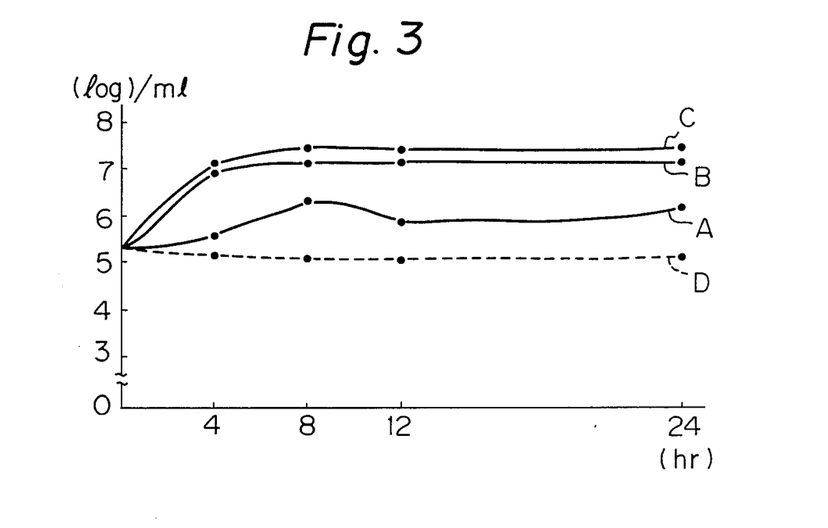
Figure 4:
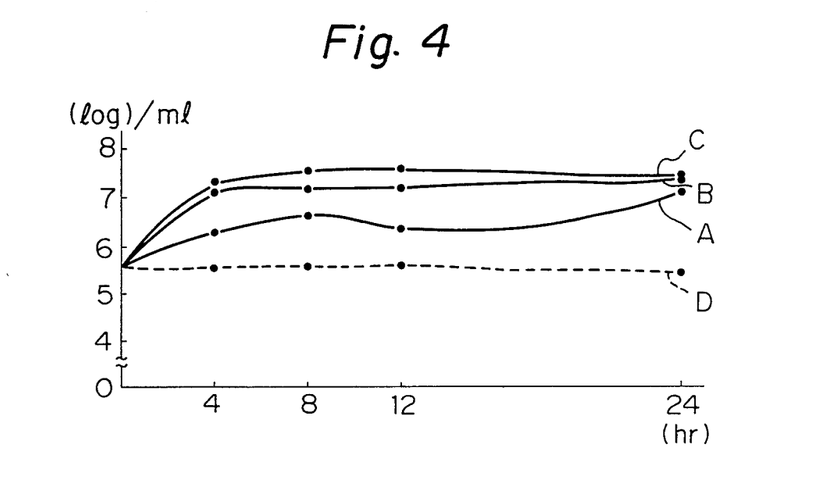
Figure 5:
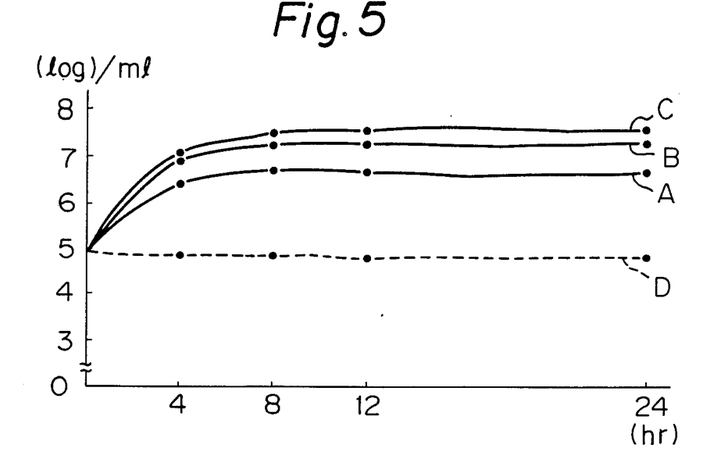
Figure 6:
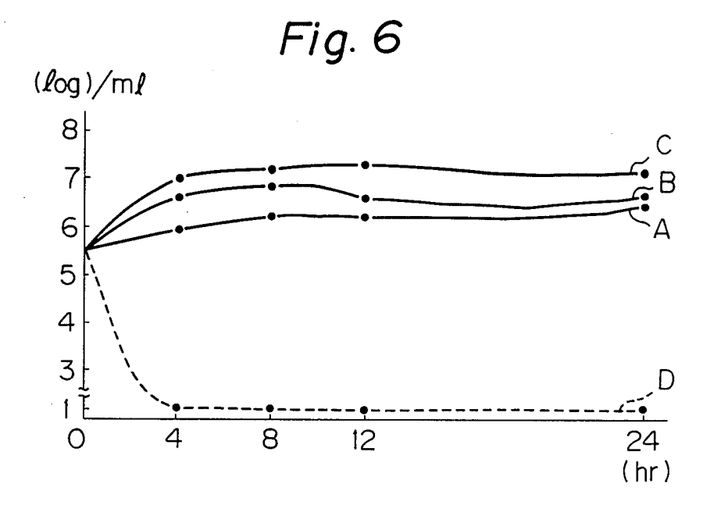
Figure 7:
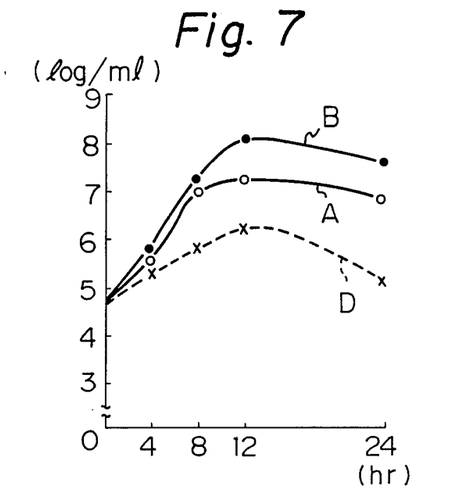
Figure 8:
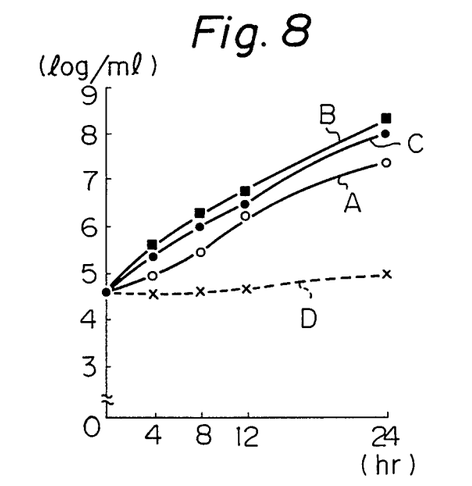
Figure 9:
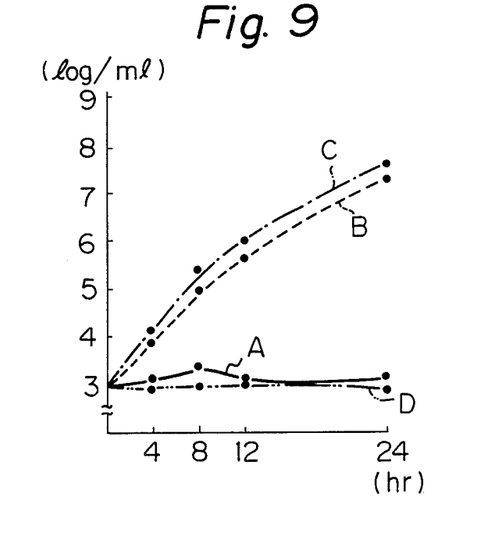
Figure 10:
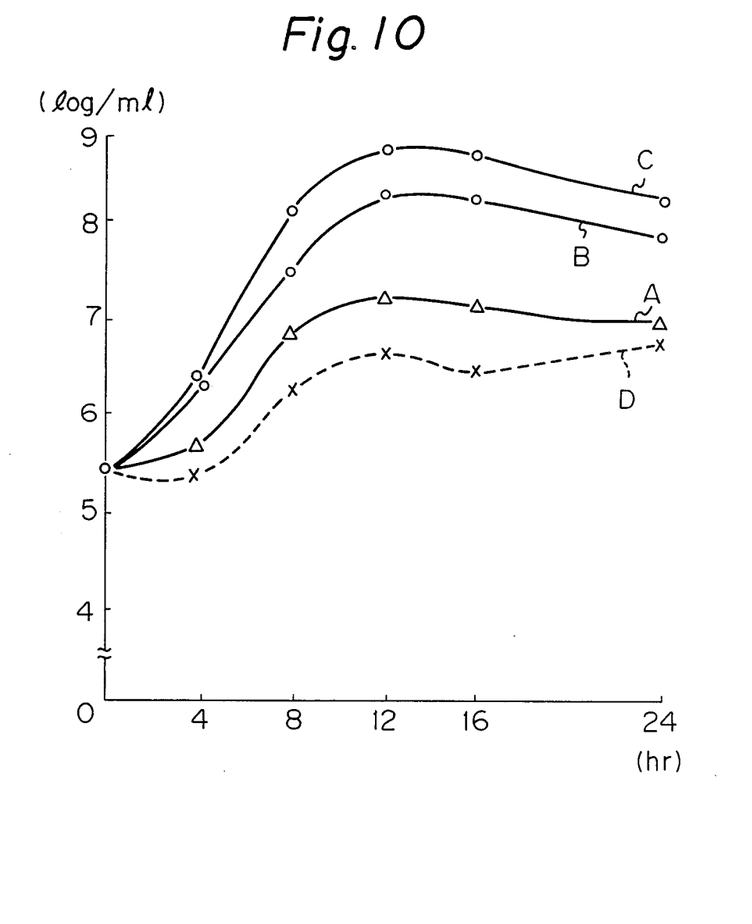
Figure 11:
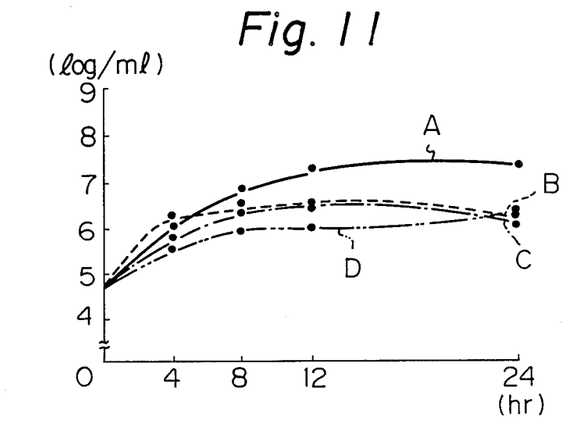
Figure 12:
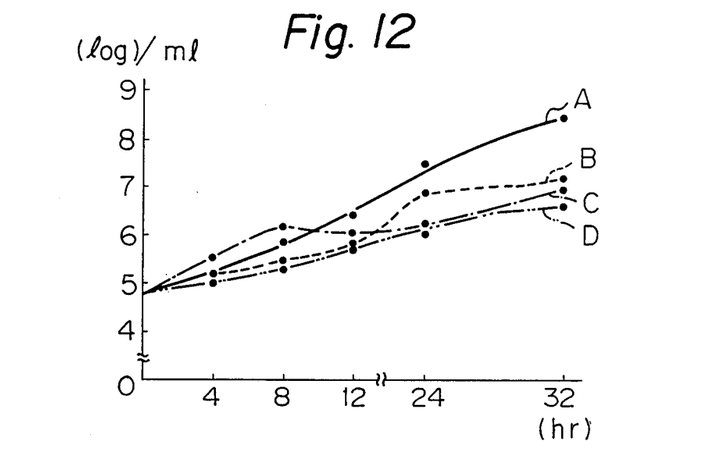
Figure 13:
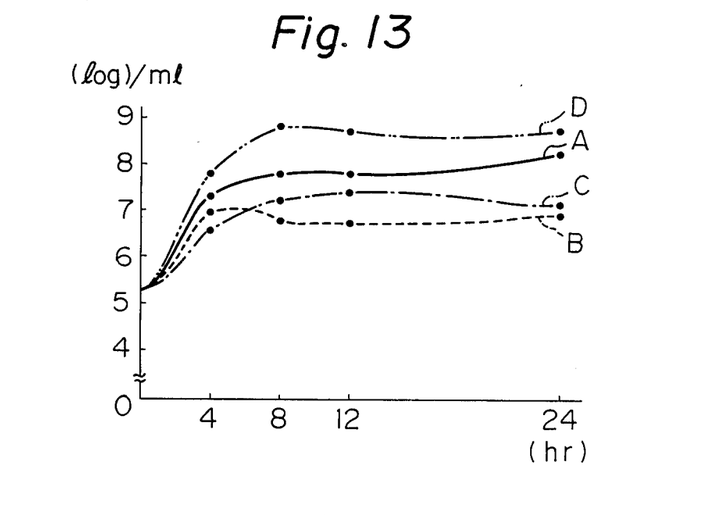
Figure 14:
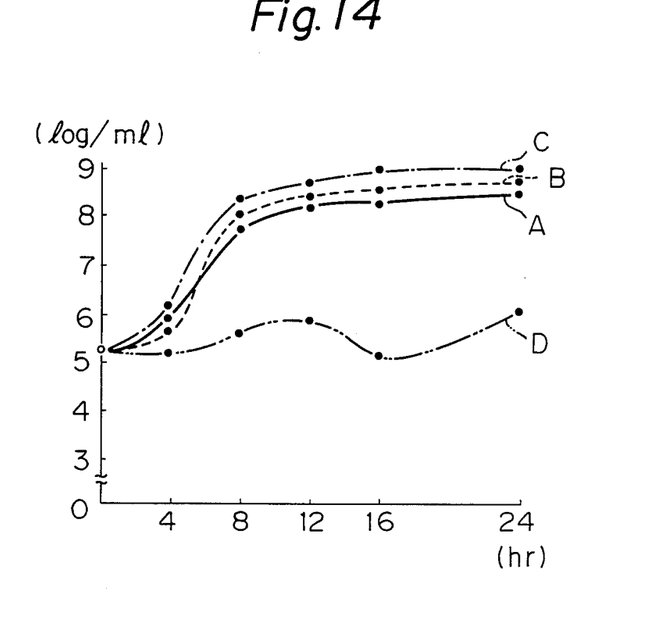
Figure 15:
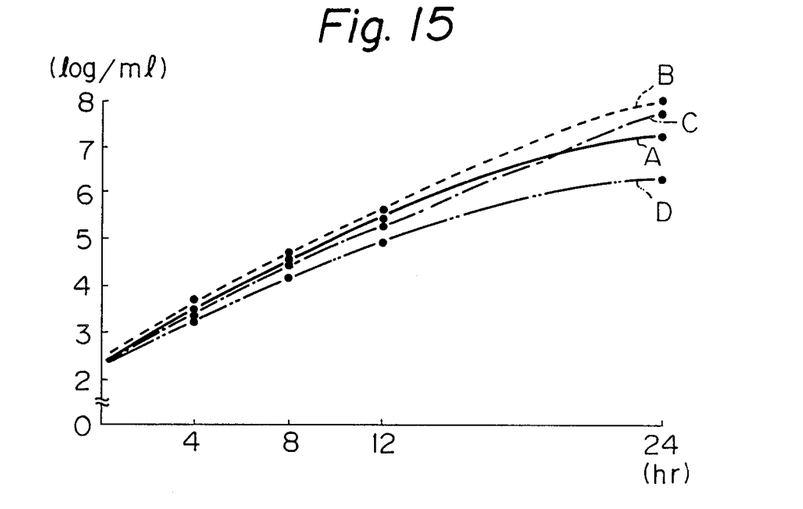
Figure 16:
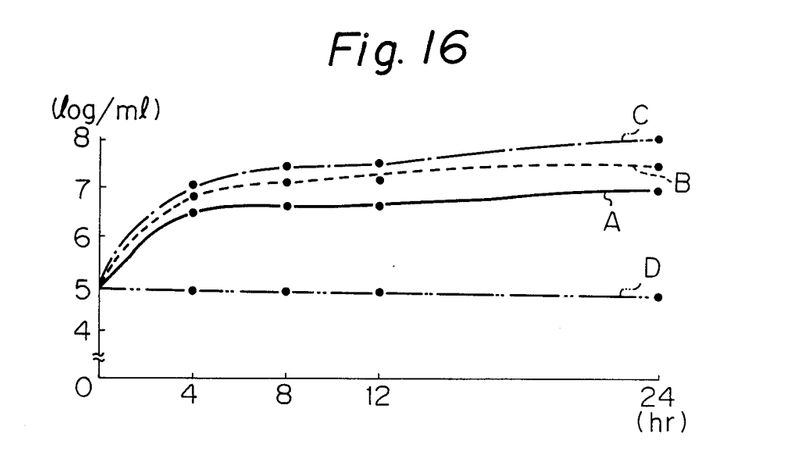
Figure 17:
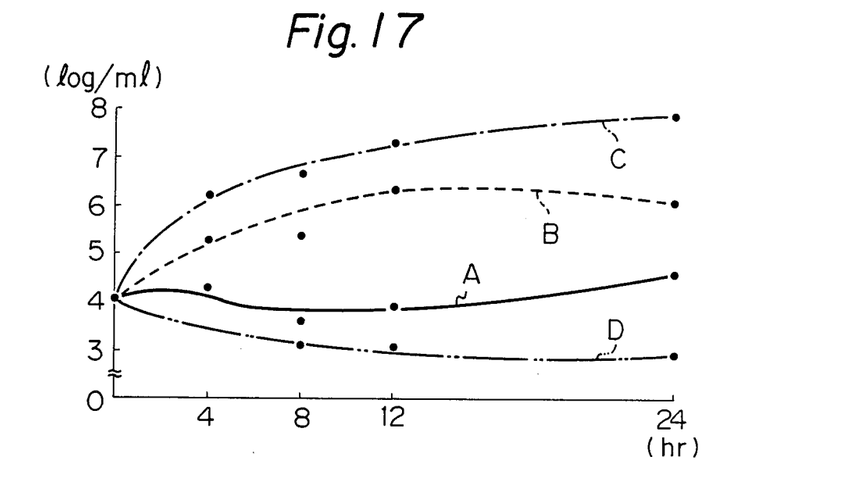
Figure 18:
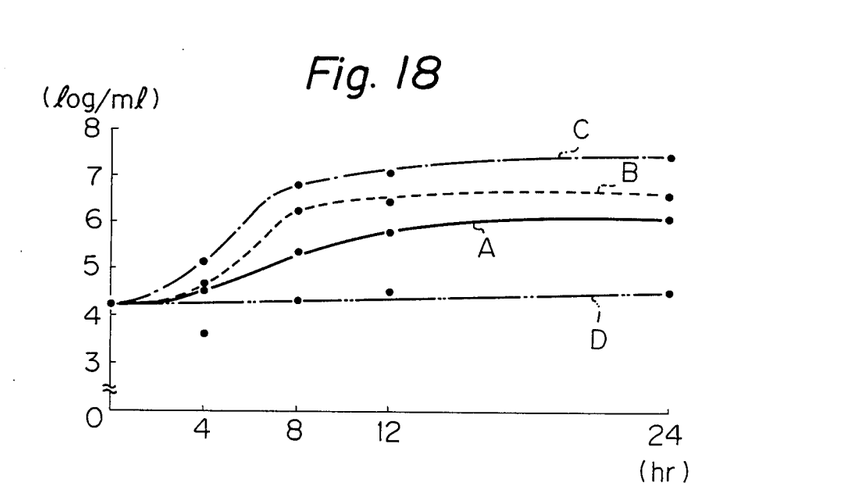

The growth-stimulating effect of the lyophilized powder of S. faecium ADV 1009, prepared according to the methods described in Example 1, was also examined. As illustrated in FIGS. 16 to 18, the results were almost the same as those of S. faecalis ADV9001.

In FIGS. 1 to 18, the ordinate indicates viable cell counts (log/ml), and the abscissa indicates the incubation time (hr). The bacterial strains used and signs (A, B, C, and D) were those shown in Table 4.

As clearly shown in each Figure, the microbial strains listed above were greatly stimulated in their growth by the addition of the lyophilized powder prepared as shown above of S. faecium ADV1009 and S. faecalis ADV1009.

TABLE 4

| FIG. | Strains | A | B | C | D |
|---|---|---|---|---|---|
| 1 | S. faecalis ADV9001 | "Powder"* of S. faecalis ADV9001 was added (1 mg/ml) | "Powder" of S. faecalis ADV9001 was added (5 mg/ml) | "Powder" of S. faecalis ADV9001 was added (10 mg/ml) | No "powder" was added |
| 2 | S. faecalis ADV9002 | | | | |
| 3 | S. faecalis ADV1003 | | | | |
| 4 | S. avium ADV2002 | | | | |
| 5 | S. durans ADV3001 | | | | |
| 6 | S. bovis ADV4002 | | | | |
| 7 | L. salivarius | | | | |
| 8 | L. casei | | | | |
| 9 | L. acidophilus | | | | |
| 10 | B. adolescentis | | | | |
| 11 | L. salivarius | | "Powder" of Bacteroides was added (1 mg/ml) | "Powder" of E. coli was added (1 mg/ml) | Yeast extract was added (1 mg/ml) |
| 12 | L. casei | | | | |
| 13 | S. faecalis ADV9001 | | | | |
| 14 | B. adolescentis | Same powder above was added (5 mg/ml) | Same powder above was added (5 mg/ml) | Same powder above was added (5 mg/ml) | Same powder above was added (5 mg/ml) |
| 15 | L. acidophilus | | | | |
| 16 | S. faecalis ADV9001 | "Powder" of S. faecium ADV1009 was added (1 mg/ml) | "Powder" of S. faecium ADV1009 was added (5 mg/ml) | "Powder" of S. faecium ADV1009 was added (10 mg/ml) | No "Powder" was added. |
| 17 | S. avium ADV2001 | | | | |
| 18 | S. facium ADV1003 | | | | |

*Powder: heat-treated and lyophilized powder according to methods described in Example 1.

EXAMPLE 3

Growth-Stimulating Effect 2

Figure 19:
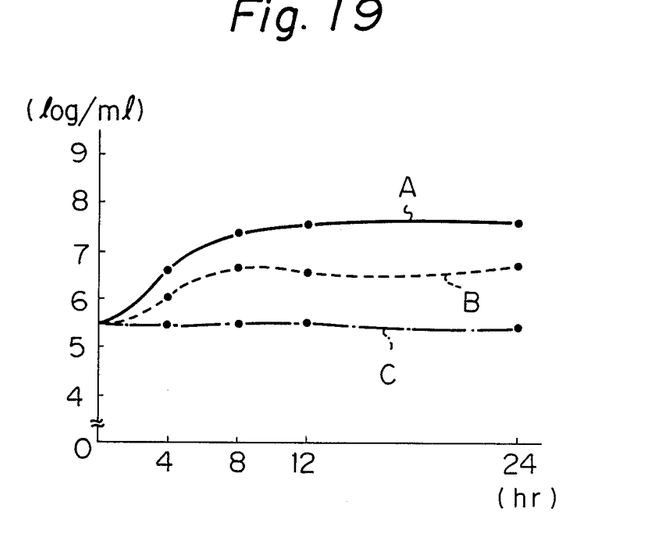

The growth-stimulating effect of the hot-water soluble extracts obtained from S. faecium ADV1009 on S. faecalis ADV9001 was examined. The bacterial powder prepared according to the above-mentioned methods of S. faecium ADV1009 was suspended (5 mg powder/ml) in PBS. The suspension was heated at 115° C. for 10 min to destroy the cells and to extract hot-water soluble components. The heat-treated suspension was centrifuged at 3,000 rpm for 15 min, and the precipitation was suspended again in PBS. These two preparations were used for media in which S. faecalis ADV9001 was inoculated. The viable cell number was counted periodically (FIG. 19). In the Figure, A and B show the growth in media into which the supernatant and the precipitation were added, respectively, and C shows the growth in PBS as a medium. The ordinate and the abscissa show viable cell counts (log/ml) and incubation time (hr). The supernatant tended to stimulate the growth of those bacterial strains as well as the heat-treated and lyophilized bacterial powder mentioned above in the examples, and the precipitate comparatively weakly stimulated the growth.

EXAMPLE 4

Clinical Tests

The bacterial powder of Streptococcus faecalis ADV9001 prepared in Example 1 was orally administered (60 mg/day) into a familial hyperlipidemic volunteer (male, 29 year-old) and normal volunteers (male, 23–42 year-old). The fecal microflora (total bacteria, Streptococcus, Lactobacillus, Bifidobacterium, Bacteroides, Enterobacteriaceae, Staphylococcus, Clostridium (lecithinase-positive), and fungi) in all the volunteers was examined. The results were shown in FIG. 20 (values of a hyperlipidemic volunteer) and FIG. 21 (average values of normal volunteers). In the Figures, A, B, C, D, and E show the viable counts of total bacteria, Streptococcus, Lactobacillus, Bifidobacterium, Bacteroides, and Enterobacteriaceae, respectively, the ordinate and the abscissa indicate viable counts (log/g) and administration period (weeks), respectively. An arrow on the abscissa indicates the start of administration. The viable cell number of Staphylococcus, Clostridium, and fungi was not shown in these Figures, because there was no significant difference between before and after the powder-administration in every volunteer.

Figure 20:
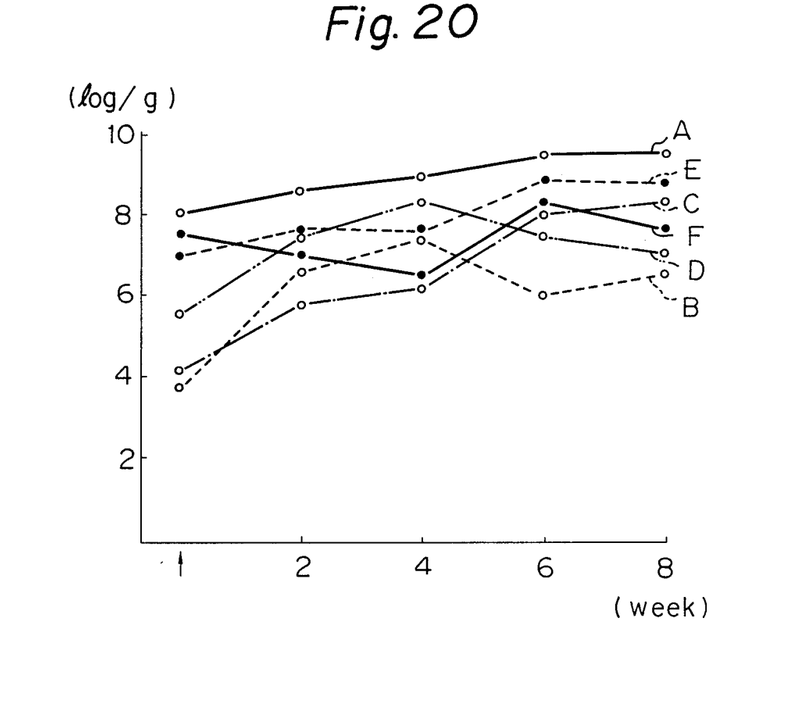
Figure 21:
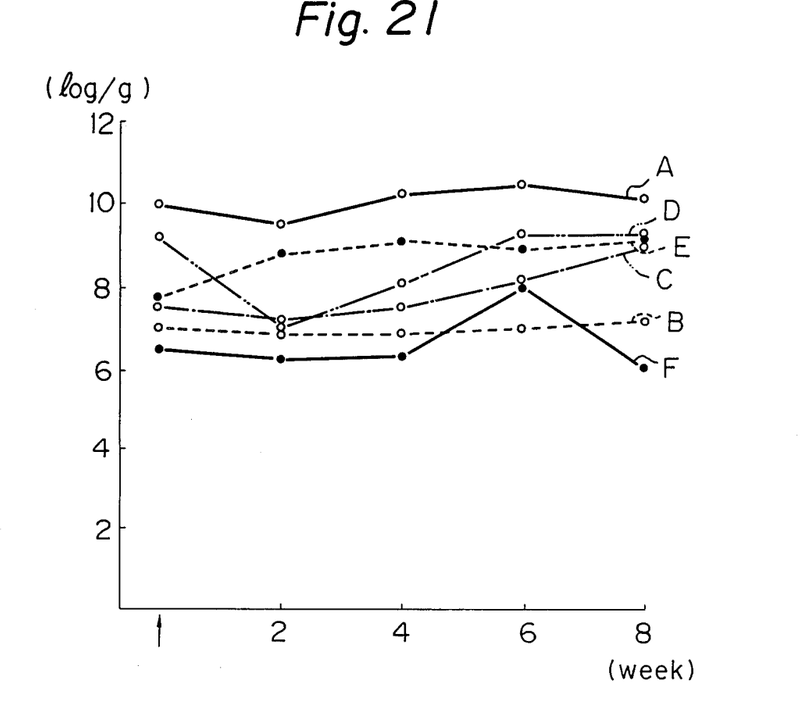

It is clear in FIG. 20 that the viable cell number of the lactic acid bacteria such as Bifidobacterium, Lactobacillus, Streptococcus, etc. which was in extremely low number in the hyperlipidemic volunteer's feces, compared with that in normal controls, increased up to that of normal controls, and the total viable cell number also increased, 8 weeks after starting of the administration.

Moreover, clinical tests similar to these mentioned above were done with the heat-treated and lyophilized powder of S. faecium ADV1009 and S. avium AD2003, and almost the same results were obtained.

EXAMPLE 5

Acute Toxicity

The heat-treated bacterial cells and hot-water soluble extracts obtained from the 7 strains of the genus Streptococcus, prepared according to the above-mentioned preparation methods were intraperitoneally administered into ICR mice (6 week-old, average body weight of $30.0 \pm 0.6$ g). Thus, the thanatobiological observation of the mice was carried out for 14 days. The $LD_{50}$ values calculated according to the Behrens-Kärber method are shown in Table 5 (heat-treated cells) and Table 6 (hot-water soluble extracts). All the strains tested of the present invention were nontoxic, substantially, in the case of daily oral administration.

TABLE 5

| Strains | $LD_{50}$ (bacterial cells/mouse) |
|---|---|
| S. faecium ADV1009 | $6.3 \times 10^9$ |
| S. faecalis ADV9001 | $3.8 \times 10^9$ |
| S. avium AD2003 | $4.2 \times 10^9$ |
| S. salivarius ADV10001 | $3.6 \times 10^9$ |
| S. durans ADV3001 | $8.9 \times 10^9$ |
| S. mitis ADV7001 | $6.7 \times 10^9$ |

TABLE 5-continued

| Strains | LD$_{50}$ (bacterial cells/mouse) |
|---|---|
| S. equinus ADV8001 | 6.5 × 10$^9$ |

Table

| Strains | LD$_{50}$ (mg/mouse) |
|---|---|
| S. faecium ADV1009 | 7.1 |
| S. faecalis ADV9001 | 6.8 |
| S. avium AD2003 | 7.2 |
| S. salivarius ADV10001 | 6.3 |
| S. durans ADV3001 | 10.1 |
| S. mitis ADV7001 | 8.6 |
| S. equinus ADV8001 | 8.2 |

Regarding pharmaceutical preparations, a 60 mg amount (equivalent to 6×10$^{10}$ cells) of the heat-treated and lyophilized powder of S. faecium ADV1009 cells prepared according to the above-mentioned preparation methods were uniformly mixed with 940 mg of purified starch powder and, then, the tablets were formed for oral administration. This tablet corresponds to a dosage of 10$^9$ cells/kg body weight for a human adult having a body weight of 60 kg.

A tablet obtained from 600 mg of the above-mentioned lyophilized powder by mixing with 400 mg of purified starch powder corresponds to a dosage of 10$^{10}$ cells/kg body weight.

Thus, the cell products of the present invention can be converted into the desired dosage form having a predetermined activity by mixing with pharmaceutically acceptable carriers based on the above-mentioned standard dosage.

We claim:

1. A method of selectively stimulating the growth of intestinal lactic acid bacteria, which comprises orally administering an effective amount of bacterial cells, or an extract thereof, of a microorganism belonging to the genus Streptococcus to a person recognized as being deficient in intestinal lactic acid bacteria.

2. A method for selectively stimulating the growth of intestinal lactic acid bacteria, which comprises orally administering an effective amount of bacterial cells, or an extract thereof, of a microorganism having the identifying characteristics of at least one strain selected from the group consisting of *Streptococcus faecium* FERM BP-296, *Streptococcus faecalis* FERM BP-297, *Streptococcus avium* FERM BP-298, *Streptococcus salivarius* FERM BP-299, *Streptococcus durans* FERM BP-300, *Streptococcus mitis* FERM BP-301, *Streptococcus equinus* FERM BP-302, and mutants thereof, to a person recognized as being deficient in intestinal lactic acid bacteria.

* * * * *